United States Patent [19]

Wettling et al.

[11] Patent Number: 5,274,164
[45] Date of Patent: Dec. 28, 1993

[54] PREPARATION OF ARYL CHLOROFORMATES

[75] Inventors: Thomas Wettling, Limburgerhof; Jochem Henkelmann, Ludwigshafen; Irene Troetsch-Schaller, Frankenthal; Hermann Koehler, Bobenheim, all of Fed. Rep. of Germany

[73] Assignee: BASF Aktiengesellschaft, Ludwigshafen, Fed. Rep. of Germany

[21] Appl. No.: 975,693

[22] Filed: Nov. 13, 1992

[30] Foreign Application Priority Data

Nov. 15, 1991 [DE] Fed. Rep. of Germany ....... 4137640

[51] Int. Cl.$^5$ ............................................. C07C 69/96
[52] U.S. Cl. ........................................................ 558/282
[58] Field of Search ........................................... 558/282

[56] References Cited

U.S. PATENT DOCUMENTS

| | | | |
|---|---|---|---|
| 3,170,946 | 2/1965 | Kilsheimer et al. | 558/282 |
| 3,211,776 | 10/1965 | Stephens | 558/282 |
| 4,085,129 | 4/1978 | Semler et al. | 558/282 |
| 4,366,102 | 12/1982 | Rauchschwalbe et al. | 558/282 |

FOREIGN PATENT DOCUMENTS

| | | |
|---|---|---|
| 1117598 | 7/1962 | Fed. Rep. of Germany . |
| 1213419 | 10/1966 | Fed. Rep. of Germany . |
| 2131555 | 12/1972 | Fed. Rep. of Germany . |
| 3019526 | 11/1981 | Fed. Rep. of Germany . |
| 1200768 | 8/1970 | United Kingdom . |

OTHER PUBLICATIONS

Ullmanns Encycl. of Tech. Chem.. 4 Ed., vol. 9, 381 (1925).

*Primary Examiner*—Johann Richter
*Attorney, Agent, or Firm*—Keil & Weinkauf

[57] ABSTRACT

A process for the preparation of aromatic aryl chloroformates of the general formula I $$Ar-O-\overset{O}{\underset{\|}{C}}-Cl, \quad (I)$$

in which Ar denotes an aryl radical optionally mono- to penta-substituted by $C_1-C_{20}$-alkyl, $C_2-C_{20}$-alkenyl, $C_3-C_8$-alkyl-cycloalkyl, $C_1-C_{20}$-haloalkyl, $C_1-C_{20}$-alkoxy, $C_1-C_{20}$-alkylthio, halo, cyano, $C_2-C_{20}$-alkylcarbonyloxy, $C_3-C_{20}$-carboalkoxy, formyl, $C_2-C_{20}$-dialkylamino, aryl, aryloxy, arylthio, aroyl, $C_7-C_{20}$-aralkyl, $C_7-C_{20}$-aralkoxy, arylsulfonyl and/or $C_7-C_{20}$-aralkylthio and/or optionally mono- or di-substituted by chloroformyl and/or nitro, from phosgene and phenols of the general formula II $$Ar-OH \quad (II),$$

in which Ar has the meanings stated above and optionally carries one or two hydroxy groups, wherein the reaction is carried out at a temperature of from 60° to 180° C. in the presence of an organic phosphorus compound of the general formula III $$R^2-\underset{R^3}{\overset{R^1}{\underset{|}{P}}}(R^4)_n(X)_n. \quad (III)$$

in which at least one of the radicals $R^1$, $R^2$, and $R^3$ stands, irrespective of the others, for $-NR^5R^6$ or $-O-R^7$ and $R^1$, $R^2$, $R^3$, $R^4$, $R^5$, $R^6$, $R^7$ independently denote $C_1-C_{20}$-alkyl, $C_2-C_{20}$-alkenyl, halo, aryl, or $C_7-C_{20}$-aralkyl and $R^1$ and $R^2$, $R^1$ and $R^3$, $R^2$ and $R^3$, and $R^5$ and $R^6$ each denote a saturated or unsaturated $C_2-C_5$-alkylene chain, X denotes hydroxy, aryloxy, halo, or an inorganic or organic acid anion, $R^4$ denotes hydrogen or $C_1-C_{20}$-alkyl or halo when X stands for halo, aryloxy, or aralkoxy, n is equal to 0 or 1, and $R^4$ and X can together denote oxygen or sulfur.

6 Claims, No Drawings

PREPARATION OF ARYL CHLOROFORMATES

The invention relates to a process for the preparation of aryl chloroformates by the reaction of phenols with phosgene in the presence of organic phosphorus compounds.

The reaction of alcohols or phenols with phosgene to form the corresponding chloroformates has already been disclosed (Ullmanns Enzyklopädie der technischen Chemie, 4th Edition, Vol. 9, Page 381, Verlag Chemie 1975). Whereas aliphatic alcohols can react with phosgene without added compounds, it is necessary to add substances to the reaction of phosgene with phenols, examples of such additives being compounds capable of binding the liberated hydrochloric acid.

It is possible, for example, to use inorganic bases such as aqueous caustic soda (DE-A 1,117,598, GB-A 1,200,768). These bases must be employed in at least stoichiometric amounts. This is economically unsatisfactory and creates disposal problems, since at least stoichiometric amounts of inorganic salts are produced. Moreover, the use of a two-phase system comprising water/organic solvent reduces the space-time yield of the process.

The addition of organic nitrogen bases has also been disclosed (DE-A 1,213,419 and U.S. Pat. No. 3,211,776). However, the use of these substances makes it necessary to carry out the reaction in an organic solvent or under pressure in an autoclave. This again impairs the space-time yield of the process or necessitates the use of equipment suitable for operating under pressure. The hydrochloride formed from the added amine base and the liberated hydrogen chloride must be removed from the reaction mixture, for example by washing the solution, extraction, filtration, or decantation, as otherwise the resulting hydrochloride would present problems during subsequent distillation. Such complications can be avoided by operating in the presence of a resin containing amino groups (U.S. Pat. No. 3,211,775), but this still requires a pressurized system. The additional costs of such polymeric catalysts makes the process less economical. In addition, it is no simple matter to operate a pressurized system involving phosgene and the hydrogen chloride formed.

Carboxamides such as dimethylformamide have also been recommended for use as catalytically effective substances (DE-A 2,131,555; U.S. Pat. No. 3,211,774).

In addition, it is known to use trisubstituted phosphines, phosphine oxides, and phosphonium salts in the manufacture of aromatic chloroformates (DE-A 3,019,526).

The activity of such additives is unsatisfactory.

It is thus an object of the present invention to overcome the aforementioned drawbacks.

Accordingly, we have found a novel and improved process for the preparation of aromatic aryl chloroformates of the general formula I $$\text{Ar}-\text{O}-\overset{\overset{\text{O}}{\|}}{\text{C}}-\text{Cl},\quad\text{(I)}$$

in which Ar denotes an aryl radical optionally mono- to penta-substituted by $C_1$-$C_{20}$-alkyl, $C_2$-$C_{20}$-alkenyl, $C_3$-$C_8$-cycloalkyl, $C_4$-$C_{20}$-alkyl-cycloalkyl, $C_1$-$C_{20}$-haloalkyl, $C_1$-$C_{20}$-alkoxy, $C_1$-$C_{20}$-alkylthio, halo, cyano, $C_2$-$C_{20}$-alkylcarbonyloxy, $C_3$-$C_{20}$-carboalkoxy, formyl, $C_2$-$C_{20}$-dialkylamino, aryl, aryloxy, arylthio, aroyl, $C_7$-$C_{20}$-aralkyl, $C_7$-$C_{20}$-aralkoxy, arylsulfonyl and/or $C_7$-$C_{20}$-aralkylthio and/or optionally mono- or di-substituted by chloroformyl and/or nitro, from phosgene and phenols of the general formula II $$\text{Ar}-\text{OH}\quad\text{(II),}$$

in which Ar has the meanings stated above and optionally carries one or two hydroxy groups, wherein the reaction is carried out at a temperature of from 60° to 180° C. in the presence of an organic phosphorus compound of the general formula III

in which at least one of the radicals $R^1$, $R^2$, and $R^3$ stands, irrespective of the others, for $-NR^5R^6$ or $-O-R^7$ and $R^1$, $R^2$, $R^3$, $R^4$, $R^5$, $R^6$, $R^7$ independently denote $C_1$-$C_{20}$-alkyl, $C_2$-$C_{20}$-alkenyl, halo, aryl, or $C_7$-$C_{20}$-aralkyl and $R^1$ and $R^2$, $R^1$ and $R^3$, $R^2$ and $R^3$, and $R^5$ and $R^6$ each denote a saturated or unsaturated $C_2$-$C_5$-alkylene chain, X denotes hydroxy, aryloxy, halo, or an inorganic or organic acid anion $R^4$ denotes hydrogen or $C_1$-$C_{20}$-alkyl or halo when X stands for halo, aryloxy, or aralkoxy, n is equal to 0 or 1, and $R^4$ and X can together denote oxygen or sulfur.

The process of the invention can be carried out as follows:

The phenol of the general formula II can be reacted with phosgene in the presence of a catalyst at an elevated temperature to form the chloroformate of the general formula I.

The process of the invention can be carried out continuously or batchwise. A continuous process may be carried out, for example, in a tubular reactor, a cascade of stirred vessels, a recycle reactor, or a countercurrent column.

The process of the invention can be carried out as a liquid phase reaction at temperatures ranging from 60° to 180° C. and preferably from 80° to 160° C. and more preferably from 100° to 140° C. and pressures of from 0.01 to 50 bar and preferably from 0.5 to 5 bar and more preferably under standard pressure (atmospheric pressure), preferably in homogeneous liquid phase. Homogeneous liquid phases are for example the melt of the phenol II or a solution of the phenol II in an inert solvent.

The organic phosphorus compound can be used in an amount of, say, from 0.01 to 20 mol % and preferably from 0.2 to 10 mol % and more preferably from 0.5 to 5 mol %, based on each hydroxy group of the phenol II.

The molar ratio of phosgene to phenol II is from 1:1 to 2:1 and preferably from 1:1 to 1.5:1 and more preferably from 1:1 to 1.2:1. Although the use of excesses larger than 2:1 is possible, it is not generally advisable, as it provides no further advantages. The use of less than the stoichiometric amount of phosgene is possible but not generally beneficial, since it necessitates the separation of unconverted phenol and the yield drops.

Suitable solvents are for example an aliphatic or aromatic hydrocarbon such as pentane, hexane, cyclohexane, toluene, xylene, or benzene, halogenated hydrocarbons such as trichloroethane, chlorobenzene, or dichlorobenzene, or esters such as ethyl acetate or butyl acetate or the chloroformate of the corresponding phenol.

Preferably, the reaction can be carried out either without the use of solvent, i.e. in the molten phenol alone, or with the use of a solvent comprising, for example, a chloroformate resulting from phosgenation of the said phenols. This achieves a higher space-time yield than when the reaction is carried out in the presence of a different solvent, since it is no longer necessary to remove the solvent by distillation. However, the use of a solvent can be advantageous when the melting point of the phenol used or of the corresponding chloroformate is above the desired reaction temperature, in which case the phenol would only slowly react with the phosgene, at least at the commencement of the reaction, if no solvent were used. Moreover, the presence of a solvent can simplify the control, and removal, of the heat produced by the exothermic reaction.

The reaction mixture can be worked up by, e.g., distillation. The bottoms will then contain the organic phosphorus compound which can be used for further reaction in the process of the invention.

The substituents Ar, X, $R^1$, $R^2$, $R^3$, $R^4$, $R^5$, $R^6$, and $R^7$ and the index n in the formulae I, II and III have the following meanings:

Ar
 aryl, such as phenyl, 1-naphthyl, 2-naphthyl, 1-anthryl, 2-anthryl and 9-anthryl and preferably phenyl, 1-naphthyl and 2-naphthyl and more preferably phenyl,
 aryl optionally mono- to penta-substituted by one of the following substituents:
 $C_1-C_{20}$-alkyl and preferably $C_1-C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1-C_4$-alkyl such as methyl, ethyl, n-propyl, isopropyl, n-butyl, isobutyl, sec-butyl and tert-butyl,
 $C_2-C_{20}$-alkenyl and preferably $C_2-C_8$-alkenyl such as vinyl, allyl, but-2-en-1-yl, but-2-en-1-yl, but-4-en-2-yl, pent-2-en-1-yl and 2,2-dimethyl-pent-1-en-1-yl,
 $C_3-C_8$-cycloalkyl and preferably $C_3-C_7$-cycloalkyl such as cyclopropyl, cyclobutyl, cyclopentyl, cyclohexyl, cycloheptyl and cyclooctyl and more preferably cyclopentyl, and cyclohexyl,
 $C_4-C_{20}$-alkyl-cycloalkyl and preferably $C_4-C_{12}$-cycloalkyl-alkyl such as cyclopropylmethyl, cyclobutylmethyl, cyclopentylmethyl, cyclohexylmethyl, cyclopropylethyl, cyclobutylethyl, cyclopentylethyl, cyclohexylethyl, cyclopropylpropyl, cyclobutylpropyl, cyclopentylpropyl, and cyclohexylpropyl and more preferably cyclopentylmethyl, cyclohexylmethyl, cyclopentylethyl, and cyclohexylethyl,
 $C_1-C_{20}$-haloalkyl and preferably $C_1-C_4$-haloalkyl and more preferably $C_1-C_4$-fluoroalkyl, $C_1-C_4$-chloroalkyl, and/or $C_1-C_4$-bromoalkyl such as fluoromethyl, difluoromethyl, trifluoromethyl, chloromethyl, dichloromethyl, trichloromethyl, bromomethyl, dibromomethyl, tribromomethyl, 1-chloroethyl, 2-chloroethyl, 1,1-dichloroethyl, 2,2-dichloroethyl, 1,2-dichloroethyl, and perchloroethyl,
 $C_1-C_{20}$-alkoxy and preferably $C_1-C_{12}$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, n-nonoxy, isononoxy, n-decoxy, isodecoxy, n-undecoxy, isoundecoxy, n-dodecoxy and isododecoxy and more preferably $C_1-C_8$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy,
 $C_1-C_{20}$-alkylthio and preferably $C_1-C_8$-alkyl such as methylthio, ethylthio, n-propylthio, isopropylthio, n-butylthio, isobutylthio, sec-butylthio, tert-butylthio, n-pentylthio, isopentylthio, sec-pentylthio, neopentylthio, 1,2-dimethylpropylthio, n-hexylthio, isohexylthio, sec-hexylthio, n-heptylthio, isoheptylthio, n-octylthio, isooctylthio and more preferably $C_1-C_4$-alkyl such as methylthio, ethylthio, n-propylthio, isopropylthio, n-butylthio, isobutylthio, sec-butyl and tert-butylthio,
 halo such as fluoro, chloro, bromo and iodo and preferably fluoro, chloro and bromo and more preferably chloro and bromo,
 cyano,
 $C_2-C_{20}$-alkylcarbonyloxy and preferably $C_2-C_8$-alkylcarbonyloxy such as acetyl, propionyl, butyryl, butylcarbamyloxy, pentylcarbamyloxy, hexylcarbamyloxy, and heptacarbonyloxy and more preferably acetyl, propionyl, and butyryl,
 $C_3-C_{20}$-carboalkoxy and preferably $C_3-C_8$-carboalkoxy such as carbomethoxy, carboethoxy and carbopropoxy and preferably carbomethoxy,
 formyl,
 $C_2-C_{20}$-dialkylamino and preferably di-$C_1-C_6$-alkylamino and more preferably di-$C_1-C_4$-alkylamino such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-n-methylamino, N-methyl-n-propylamino,N-methyl-N-(1-methylethyl)amino,N-butyl-n-methylamino,N-methyl-N-(1-methylpropyl)amino,N-methyl-N-(2-methylpropyl)amino, N-(1,1-dimethylethyl)-N-methylamino, N-ethyl-n-propylamino, N-ethyl-N-(1-methylethyl)amino, N-butyl-n-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-n-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino and preferably N,N-dimethylamino, N,N-diethylamino, and N,N- dipropylamino and more preferably N,N-dimethylamino, aryl, such as phenyl, 1-naphthyl, 2-naphthyl, 1-anthryl, 2-anthryl, 9-anthryl, o-tolyl, m-tolyl, and p-tolyl and preferably phenyl, o-tolyl, m-tolyl, and p-tolyl and more preferably phenyl, aryloxy such as phenoxy, 1-naphthoxy, 2-naphthoxy, 1-anthroxy, 2-anthroxy, 9-anthroxy, o-cresyl, m-cresyl, and p-cresyl, preferably phenoxyl, o-cresyl, m-cresyl, and p-cresyl and more preferably phenoxy, m-cresyl, and o-cresyl, arylthio such as phenylthio, 1-naphthylthio, 2-naphthylthio, 1-anthrylthio, 2-anthrylthio and 9-anthrylthio and preferably phenylthio, 1-naphthylthio and 2-naphthylthio and more preferably phenylthio, aroyl such as phenoyl, 1-naphthoyl, 2-naphthoyl, 1-anthroyl, 2-anthroyl and 9-anthroyl and preferably phenoyl, 1-naphthoyl and 2-naphthoyl and more preferably phenoyl, $C_7$-$C_{20}$-aralkyl and preferably $C_7$-$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl and more preferably benzyl, 1-phenethyl and 2-phenethyl, $C_7$-$C_{20}$-aralkoxy and preferably $C_7$-$C_{12}$-phenylalkoxy such as benzyloxy, 1-phenethoxy, 2-phenethoxy, 1-phenylpropoxy, 2-phenylpropoxy, 3-phenylpropoxy, 1-phenylbutoxy, 2-phenylbutoxy, 3-phenylbutoxy and 4-phenyl-butoxy and more preferably benzyl, 1-phenethoxy and 2-phenethoxy, arylsulfonyl such as phenylsulfonyl, 1-naphthylsulfonyl, 2-naphthylsulfonyl, 1-anthrylsulfonyl, 2-anthrylsulfonyl and 9-anthrylsulfonyl and preferably phenylsulfonyl, 1-naphthylsulfonyl and 2-naphthylsulfonyl and more preferably phenylsulfonyl, $C_7$-$C_{20}$-aralkylthio and preferably $C_7$-$C_{12}$-phenylalkylthio such as benzylthio, 1-phenethylthio, 2-phenethylthio, 1-phenylpropylthio, 2-phenylpropylthio, 3-phenylpropylthio, 1-phenylbutylthio, 2-phenylbutylthio, 3-phenylbutylthio and 4-phenyl-butylthio and more preferably benzylthio, 1-phenethylthio and 2-phenethylthio, and/or aryl optionally mono- or di-substituted by one of the following radicals:
chloroformyl,
nitro,
and, in the case of compounds II, additionally one or two hydroxy functions.

$R^1$, $R^2$, $R^3$, $R^5$, $R^6$, $R^7$ independently denote $C_1$-$C_{20}$-alkyl and preferably $C_1$-$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$-$C_4$-alkyl such as methyl, ethyl, n-propyl, isopropyl, n-butyl, isobutyl, sec-butyl and tert-butyl.

$C_2$-$C_{20}$-alkenyl and preferably $C_2$-$C_8$-alkenyl such as vinyl, allyl, but-2-en-1-yl, but-4-en-1-yl, but-4-en-2-yl, pent-2-en-1-yl and 2,2-dimethyl-pent-1-en-1-yl, halo such as fluoro, chlorine, bromo and iodo and preferably fluoro, chloro and bromo and more preferably chloro and bromo, aryl, such as phenyl, 1-naphthyl, 2-naphthyl, 1-anthryl, 2-anthryl, and 9-anthryl and preferably phenyl, 1-naphthyl, and 2-naphthyl and more preferably phenyl, $C_7$-$C_{20}$-aralkyl and preferably $C_7$-$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl and more preferably benzyl, 1-phenethyl and 2-phenethyl, $R^1$ and $R^2$, $R^1$ and $R^3$, $R^2$ and $R^3$, $R^5$ and $R^6$
denote a saturated or unsaturated $C_2$-$C_5$-alkylene chain, such as propanediyl, butanediyl, pentanediyl, butenediyl, and pentenediyl and preferably butanediyl and pentanediyl, x denotes
hydroxy
aryloxy such as phenoxy, 1-naphthoxy, 2-naphthoxy, 1-anthroxy, 2-anthroxy, 9-anthroxy, o-cresyl, m-cresyl, and p-cresyl and preferably phenoxy, o-cresyl, m-cresyl, and p-cresyl and more preferably phenoxy, m-cresyl, and o-cresyl, halo such as fluoro, chloro, bromo and iodo and preferably fluoro, chloro and bromo and more preferably chloro and bromo, an inorganic or organic acid anion such as a phosphonium salt, e.g., a chloride, bromide, sulfate, phosphate, methylsulfate, or an aliphatic or aromatic sulfonate, $R^4$ denotes
hydrogen,
$C_1$-$C_{20}$-alkyl and preferably $C_1$-$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$-$C_4$-alkyl such as methyl, ethyl, n-propyl, isopropyl, n-butyl, isobutyl, sec-butyl and tert-butyl, halo, such as fluoro, chloro, bromo, and iodo and preferably fluoro, chloro, and bromo and more preferably chloro and bromo, when X stands for halo, aryloxy, or aralkoxy, n is equal to 0 or 1, $R^4$ and X together stand for oxygen or sulfur.

Examples of suitable organic phosphorus compounds of formula (I) are hexamethylphosphoric triamide, tris(dimethylamino)phosphine, 1-diethylaminophospholane, ethanephosphorous diethylamide, dimethylaminodichlorophosphane, diethylamino-ethoxy-phenyl-phosphane, phosphorous bis(dimethylamide), 3-methyl-2-chloro-1,2,3-oxazaphosphorinane, phosphorous bis(dimethylamide) chloride, and triphenyl phosphite, tricresyl phosphite, chlorotetraphenoxyphosphorane and dichlorotriphenoxyphosphorane.

Examples of specific phenols II which can be used in the present invention are:
phenol, o-cresol, m-cresol, p-cresol, xylenols, 4-chlorophenol, hydroquinone, resorcinol, 1-naphthol, 2-naphthol, 1,5-dihydroxynaphthalene, 4,4'-methylenebisphenol, 1,1-bis(4-hydroxyphenyl)-ethane, 2,2-bis-(4-hydroxyphenyl)-propane, 4,4'-cyclohexylidene-bisphenol, 4,4'-dihydroxydiphenyl ether, 4,4'-dihydroxydiphenyl sulfide, 4,4'-dihydroxydiphenylsulfone, 4,4'-dihydroxydiphenyl-n-methylamine, 3-hydroxybenzophenone, and 4-hydroxybenzophenone.

Suitable aryl chloroformates which can be prepared by the process of the invention are, for example:

phenyl chloroformate, o-cresyl chloroformate, m-cresyl chloroformate, p-cresyl chloroformate, dimethylphenyl chloroformate, 4-chlorophenyl chloroformate, naphthyl chloroformate, hydroquinone chloroformate, resorcinol chloroformate, 1,5-dihydroxynaphthalene-bis-chloroformate, 4,4'-methylenebisphenyl chloroformate, 1,1-bis(4-hydroxyphenyl)-ethane chloroformate, 2,2-bis-(4-hydroxyphenyl)-propane chloroformate, 4,4'-cyclohexylidenebisphenyl chloroformate, 4,4'-dihydroxydiphenyl ether bis-chloroformate, benzophenone-4-chloroformate.

The aryl chloroformates, particularly the phenyl chloroformates, are obtained to a high degree of purity by the method proposed in the present invention. They are therefore suitable for use as starting points for various applications. They can, of course, be further purified in known manner, for example by distillation or recrystallization.

Aryl chloroformates are valuable intermediates, for example for the preparation of dyes such as Sirius dyes (DE-A 2,325,088, Ullmanns Enzyklopädie der technischen Chemie, Vol. 4, Pages 105, 108 and 109, Urban und Schwarzenberg, 3rd Edition, Berlin/Munich, 1953), for the preparation of polycarbonate plastics and plant protectants, and for the preparation of bactericides. These applications are known to the person skilled in the art and are described in DE-A 2,131,555, DE-A 1,213,419 and Ullmanns Enzyklopädie der technischen Chemie, 4th Edition, Vol. 9, Page 383, Verlag Chemie 1975.

EXAMPLES

Comparative Examples

EXAMPLE 1

(Carried out in a manner similar to that described in DE-A 2,131,555, Example 2)

A mixture of 100 g of phenylchloroformate and 3.7 g (0.05 mol) of N,N-dimethylformamid is placed in a round flask equipped with a stirrer, a thermometer, a phosgene inlet tube, a heated drip funnel and a condenser filled with dry ice and acetone and is heated to 120° C., and 112 g (1.13 mol) of phosgene are metered in, together with 94 g (1 mol) of phenol, over a period of 4 hours. The reaction is allowed to continue for 1 hour at the same temperature, after which the condenser is removed and the excess phosgene is blown out by bubbling nitrogen through the reaction mixture. A black mixture is obtained, from which by-products of the reaction are deposited on to the inner surface of the flask in the form of a black layer.

The crude product possesses a phenyl chloroformate content of 97.9% and a diphenyl carbonate content of 1.8% (GC analysis). The product mixture is distilled and the phenyl chloroformate distills at about 85° C. and 20 torr. Gas-chromatographic analysis shows that the distilled product still contains distinct traces of impurities, which can be removed by distillation not without considerable difficulty.

EXAMPLE 2

(Carried out in a manner similar to that described in DE-A 3,019,526, Example 4)

100 g of phenyl chloroformate and 2.6 g (0.01 mol) of triphenylphosphine are placed in an apparatus as described in Example 1. 113 g (1.13 mol) of phosgene and 94 g (1 mol) of phenol are metered in at a reaction temperature of 120° C. over a period of 4 hours. The reaction is allowed to continue for 1 hour, after which excess phosgene is blown out and there is obtained a clear pale yellow crude product having a phenyl chloroformate content of 97.6 % and a diphenyl carbonate content of 1.7% (GC analysis). The product mixture is distilled to give residues containing solid particles.

Examples of the invention:

EXAMPLE 3

The experiment is carried out in a manner similar to that described in Example 1 and using similar equipment. 94 g (1 mol) of phenol are reacted with phosgene in the presence of 3.1 g (0.01 mol) of triphenyl phosphite over a period of 4 hours at 120° C. There is obtained a clear pale yellow crude product having a phenyl chloroformate content of 98.3% and a diphenyl carbonate content of 1.4% (GC analysis). Following distillation there is obtained a water-clear phenyl chloroformate, which contains no impurities, as determined by GC analysis.

EXAMPLE 4

The reaction is carried out as described in Example 3 but using 6.2 g (0.02 mol) of triphenyl phosphite as catalyst. Following a reaction time of only 1.5 hours and a post-reaction time of 1 hour there is obtained a pale yellow clear crude product having a phenyl chloroformate content of 98.5% and a diphenyl carbonate content of 1.2% (GC analysis).

EXAMPLE 5

The reaction is carried out as described in Example 3 but using 9.0 g (0.05 mol) of hexamethylphosphoric triamide as catalyst. Following a reaction time of 4 hours and a post-reaction time of 1 hour there is obtained a pale yellow clear crude product having a phenyl chloroformate content of 95.7% and a diphenyl carbonate content of 2.5% (GC analysis).

EXAMPLE 6

The reaction is carried out as described in Example 3 but using the bottoms obtained after distillation in Example 5 as catalyst. Following a reaction time of 2 hours and a post-reaction time of 1 hour there is obtained a pale yellow clear crude product having a phenyl chloroformate content of 89.2% and a diphenyl carbonate content of 6.9% (GC analysis).

EXAMPLE 7

The reaction is carried out as described in Example 3 but using 8.2 g (0.05 mol) of hexamethyltriaminophosphine as catalyst. Following a reaction time of 2.5 hours and a post-reaction time of 1 hour there is obtained a dark-colored crude product having a phenyl chloroformate content of 84.5% and a diphenyl carbonate content of 1.3% (GC analysis).

EXAMPLE 8

The reaction is carried out as described in Example 4 but without using any phenyl chloroformate and using only 6.2 g (0.02 mol) of triphenyl phosphite. Following a reaction time of 5.5 hours there is obtained a clear pale yellow crude product having a phenyl chloroformate content of 97.6% and a diphenyl carbonate content of 1.9% (GC analysis).

EXAMPLE 9

The reaction is carried out as described in Example 4 but using only 10 g of phenyl chloroformate and 6.2 g (0.02 mol) of triphenyl phosphite. Following a reaction time of 4.5 hours there is obtained a clear pale yellow crude product having a phenyl chloroformate content of 97.8% and a diphenyl carbonate content of 1.5% (GC analysis).

EXAMPLE 10

The reaction is carried out as described in Example 4 but using 10 g of phenol and 6.2 g (0.02 mol) of triphenyl phosphite. Following a reaction time of 2.5 hours there is obtained a clear pale yellow crude product having a phenyl chloroformate content of 95.5% and a diphenyl carbonate content of 3.8% (GC analysis).

EXAMPLE 11

The reaction is carried out as described in Example 3 but using 17.5 g (0.04 mol) of chlorotetraphenoxyphosphorane as catalyst. Following a reaction time of 1 hour and a post-reaction time of 1 hour there is obtained a clear pale yellow crude product having a phenyl chloroformate content of 92.6% and a diphenyl carbonate content of 2.9% (GC analysis).

EXAMPLE 12

22 g (0.2 mol) of m-cresol and 6.3 g (0.02 mol of triphenyl phosphite are placed in an apparatus as described in Example 1. 194 g (1.8 mol) of m-cresol, 11.3 g (0.035 mol) of triphenyl phosphite, and 220 g (2.2 mol) of phosgene are metered in at a reaction temperature of 120° C. over a period of 4 hours. The reaction is allowed to continue for 1 hour, after which excess phosgene is blown out and there is obtained a clear brown crude product having an m-cresyl chloroformate content of 91% and a carbonate content of 1.4% (GC analysis).

EXAMPLE 13

The reaction is carried out as described in Example 12 but using 19.4 g (0.055 mol) of tri-m-cresyl phosphite as catalyst. Following a reaction time of 2 hours and a post-reaction time of 1 hour there is obtained a clear yellow product having an m-cresyl chloroformate content of 97.2% and a carbonate content of 1.8% (GC analysis).

EXAMPLE 14

157 g of phenyl chloroformate and 6.3 g (0.02 mol) of triphenylphosphite are placed in continuous facilities comprising metering means, a main reactor equipped with stirrer, phosgene inlet tube, and overflow, and further comprising a secondary reactor equipped with stirrer and a continuous stripping column. In both the main and secondary reactors, the temperature is maintained at 125° C. The automatic metering means cause the dropwise addition of 1 mol/h of phenol containing 0.02 mol of dissolved triphenyl phosphite whilst concurrently introducing sufficient phosgene to maintain an excess thereof (ca 1.2 mol/h), such that the reaction temperature remains constant.

After the starting phase, this continuous setup produces a crude product having a phenyl chloroformate content of 98.6% and a diphenyl carbonate content of 1.2% (GC analysis).

We claim:

1. A process for the preparation of aromatic chloroformates of the formula I

in which Ar denotes an aryl radical optionally mono- to penta-substituted by $C_1$-$C_{20}$-alkyl, $C_2$-$C_{20}$-alkenyl, $C_3$-$C_8$-cycloalkyl, $C_4$-$C_{20}$-alkylcycloalkyl, $C_1$-$C_{20}$-haloalkyl, $C_1$-$C_{20}$-alkoxy, $C_1$-$C_{20}$-alkylthio, halo, cyano, $C_2$-$C_{20}$-alkylcarbonyloxy, $C_3$-$C_{20}$-carboalkoxy, formyl, $C_2$-$C_{20}$-dialkylamino, aryl, aryloxy, arylthio, aroyl, $C_7$-$C_{20}$-aralkyl, $C_7$-$C_{20}$-aralkoxy, arylsulfonyl and/or $C_7$-$C_{20}$-aralkylthio and/or optionally mono- or di-substituted by chloroformyl and/or nitro, from phosgene and phenols of the formula II

in which Ar has the meanings stated above and optionally carries one or two hydroxy groups, wherein the reaction is carried out at a temperature of from 60° to 180° C. in the presence of an organic phosphorus compound of the formula III

in which $R^7$ is aryl or $C_7$-$C_{20}$-aralkyl in a liquid phase.

2. A process as claimed in claim 1, wherein the organic phosphorus compound used is triphenyl phosphite, or tricresyl phosphite.

3. A process as claimed in claim 1, wherein the organic phosphorus compound III is used in a concentration of from 0.1 to 20 mol % per equivalent of organic hydroxyl group in the phenol.

4. A process as claimed in claim 1, wherein the reaction is carried out at a temperature of between 80° and 160° C.

5. A process as claimed in claim 1, wherein the reaction is carried out in the presence of an inert solvent.

6. A process as claimed in claim 1, wherein an inert solvent is used which comprises the aromatic chloroformate to be prepared.

* * * * *

UNITED STATES PATENT AND TRADEMARK OFFICE
CERTIFICATE OF CORRECTION

PATENT NO.: 5,274,164

DATED: December 28, 1993

INVENTOR(S): WETTLING et al.

It is certified that error appears in the above-identified patent and that said Letters Patent is hereby corrected as shown below:

In the Abstract, column 2, line 3, "$C_3$-$C_8$-alkyl-cycloalkyl" should read --$C_3$-$C_8$-cycloalkyl, $C_4$-$C_{20}$-alkyl-cycloalkyl--.

Signed and Sealed this

Fourth Day of October, 1994

Attest:

BRUCE LEHMAN

Attesting Officer

Commissioner of Patents and Trademarks